(12) United States Patent
Akiba (10) Patent No.: US 6,425,535 B1
(45) Date of Patent: Jul. 30, 2002

(54) FLUID SUPPLYING APPARATUS FOR ENDOSCOPE

(75) Inventor: Haruo Akiba, Omiya (JP)

(73) Assignee: Fuji Photo Optical Co., Ltd., Omiya (JP)

( * ) Notice: Subject to any disclaimer, the term of this patent is extended or adjusted under 35 U.S.C. 154(b) by 28 days.

(21) Appl. No.: 09/629,875

(22) Filed: Aug. 1, 2000

(30) Foreign Application Priority Data

Aug. 2, 1999 (JP) .......................................... 11-218285

(51) Int. Cl.$^7$ ............................................ A61M 11/02
(52) U.S. Cl. ...................... 239/369; 239/407; 239/414; 239/346; 600/158; 600/159; 134/21
(58) Field of Search ............................. 239/369, 373, 239/398, 407, 414, 419.5, 270, 310, 346; 600/158, 159, 157, 156; 604/265, 266, 267; 134/104.1, 113, 100.1, 21

(56) References Cited

U.S. PATENT DOCUMENTS

| | | | | |
|---|---|---|---|---|
| 4,281,646 A | * | 8/1981 | Kinoshita | .................... 600/157 |
| 4,525,220 A | * | 6/1985 | Sasa et al. | ..................... 134/21 |
| 4,537,209 A | * | 8/1985 | Sasa | ........................ 134/102.1 |
| 5,575,756 A | * | 11/1996 | Karasawa et al. | .......... 600/157 |
| 5,630,795 A | * | 5/1997 | Kuramoto et al. | .......... 600/157 |
| 5,795,404 A | * | 8/1998 | Murphy et al. | ................ 134/21 |

FOREIGN PATENT DOCUMENTS

EP 0075153 * 3/1983

* cited by examiner

Primary Examiner—William C. Doerrler
Assistant Examiner—Dinh Q. Nguyen
(74) Attorney, Agent, or Firm—Oblon, Spivak, McClelland, Maier & Neustadt, P.C.

(57) ABSTRACT

A nozzle spraying a cleaning liquid to an observation window. A jet spray aperture for spraying fluid is provided to the distal end portion of an insertion portion. A first fluid supplying passage connected to a nozzle and a control-valve. A second fluid supplying passage connected to the jet spray aperture. A casing divides the first fluid supplying passage into a nozzle side passage and a valve side passage, connects to the second fluid supplying passage, and includes a pump connector detachably connected to the fluid pumping means and a supplying passage. A switching passage, formed in the pump connector, switches between positions wherein the nozzle side passage is connected to or cut off from the valve side passage, depending on the state of the supplying passage. A check valve is provided to the supplying passage for preventing flow from the switching passage side to the supplying passage side.

8 Claims, 7 Drawing Sheets

FLUID SUPPLYING APPARATUS FOR ENDOSCOPE

DETAILED DESCRIPTION OF THE INVENTION

1. Field of the Invention

The present invention relates to a fluid supplying apparatus for an endoscope, and particularly relates to a fluid supplying apparatus comprising a nozzle for performing cleaning of an observation window and a jet spray aperture, and arranged so as to spray cleaning liquid from the nozzle at a desired pressure and spray a desired fluid from the jet spray aperture.

2. Description of the Related Art

Generally, as fluid supplying apparatus for endoscopes, there are lens surface cleaning devices for supplying cleaning liquid and pressurized air to an observation window provided at a distal end of an insertion portion in the event that the lens surface mounted to the observation window is soiled with body fluids or the like. As is known, the lens surface cleaning device has a nozzle opening toward the observation window, a liquid supplying passage and air passage connected to the nozzle. Also, a control valve is provided at an operating unit provided continuously from the insertion portion, in order to perform fluid supply control from the liquid supplying passage and air passage to the nozzle. In addition to the lens surface cleaning, there is the need to supply other fluids into the body. For example, when body fluids or other stains adhere to the walls of the body cavity, observation with the endoscope is difficult, and also in the event that there is a substantially great amount of adhesion, observation may be impossible. However, the nozzle for cleaning the lens surface is directed at a certain angle relative to the lens surface, i.e., in the direction across the field of view of the observation window, so spraying cleaning liquid from this direction cannot wash the body cavity wall to be observed. Accordingly, a jet spray aperture is opened at the distal end of the insertion portion for spraying fluid directly toward the direction of the observation field of the view of the observation window.

The fluid supplying passage for supplying fluid to the jet spray aperture is extended to the operating unit, and is connected to a pump connector provided to the operating unit. Detachably connected to this pump connector is a fluid pumping means, such as syringes or the like. Accordingly, a syringe, for example, consisting of an outer cylinder, a piston slidably provided within this outer cylinder, and an inner cylinder to cause the piston sliding movement within the outer cylinder is connected to the pump connector. Pushing the syringe piston into the outer cylinder supplies fluid or the like therein to the jet spray aperture.

Now, in order to perform jet spraying, the syringe or other pumping means must be operated manually. However, it is essentially impossible for a doctor or other operator rasping the operating unit of the endoscope to operate the fluid pumping means, and requires the assistance of a nurse or the like for this operation. It is known that cleaning liquid for the lens surface is supplied to the jet spraying aperture, such as disclosed in Japanese Unexamined Patent Application Publication No. 6-68717, so as to eliminate the need for assistance of a nurse or the like on jet spraying.

With this known fluid supplying apparatus, a three-way valve is provided to the operating unit, and a passage at the fluid source side and two passages consisting of a nozzle side and an aperture slide passages are each connected to the casing of the three-way valve. Then, the valve member of this three-way valve is mounted to the operating unit in a manner capable of being reciprocally rotated by a predetermined angle. Accordingly, rotating the valve member switches between a state wherein the fluid source passage is communicated to the nozzle side passage, and a stat wherein this is connected to the aperture side passage. Consequently, when stain or the like is adhered to the body cavity wall, by rotating the valve member of the three-way valve, the fluid source is connected to the jet spray aperture, thereby supplying the cleaning liquid from the fluid source to the jet spray aperture. Once the stain is removed from the body cavity wall, the valve member of the three-way valve may be operated to return to the state that the fluid source side is connected to the nozzle side for restoring a state wherein normal lens surface cleaning may be performed. Further, effectively removing stain adhered to the body cavity wall requires a pressure higher than that for lens surface cleaning, so with the above-described conventional art, the supplying pressure of the cleaning liquid from the fluid source is raised.

Now, the conditions for cleaning liquid supplying are not always the same for the above-described two states. That is, stain of the lens surface can often be easily removed with a smaller amount of cleaning liquid at a lower pressure, as compared to the removing of stain adhered to the body cavity wall. Further, the lens surface is constantly being soiled, so lens surface cleaning is repeatedly performed during operation. In the event that lens surface cleaning is performed at an unnecessarily high pressure, the amount of flow increases to force much pain to the patient. Accordingly, at the time of performing lens surface cleaning, the amount of cleaning liquid must be kept to an absolute minimum. On the other hand, a rather high pressure is necessary for jet spraying. Accordingly, the supplying pressure and supplying amount of cleaning liquid differs between lens surface cleaning and body cavity wall cleaning, so using the same fluid source is not necessarily desirable. However, depending on the state and the like of stain adhered to the lens surface, there are cases wherein spraying high-pressure cleaning liquid is desired. Thus, a configuration wherein selection can be made of spraying the cleaning liquid at a high pressure as necessary on cleaning the lens surface cleaning, is further preferable.

Also, the fluid supplied toward the body cavity wall is not limited to the above cleaning liquid, and for example, coloring agents or the like may be dispersed on or sprayed onto the body cavity wall. However, as described above, in the event that the configuration is such that the jet spray aperture is connected to the fluid source for lens surface cleaning liquids other than cleaning liquid cannot be supplied to the jet spray aperture. Accordingly, yet another fluid supplying passage must be provided in other to perform coloring agent dispersion, drug fumigation, etc.

SUMMARY OF THE INVENTION

The present invention has been made in light of the above points, and accordingly it is an object thereof to allow desire fluids to be supplied to the observation window and jet spray aperture at desired pressures and desired flows.

In order to achieve the above objects, according to the present invention, there is provided a fluid supplying apparatus for an endoscope, which comprises: an observation window provided at a distal end portion of an insertion portion; a nozzle for spraying at least a cleaning liquid toward the observation window; a first fluid supplying passage connected to the nozzle; a jet spray aperture formed to the distal end portion for spraying fluid in forward direction of the insertion portion; a second fluid supplying passage connected to the jet spray aperture; a control valve provided within a operating unit connected to the insertion portion, to which the first fluid supplying passage is connected; a casing for dividing the first fluid supplying passage into a nozzle side passage and a valve side passage, and to which the second fluid supplying passage is connected; a pump connector, provided within the casing, for detachably mounting a fluid pumping means and being formed a supplying passage for flowing fluid from the fluid pumping means; a switching passage provided to the pump connector, the switching passage being capable of switching between a first position wherein the nozzle side passage is connected to a valve side passage of the first fluid supplying passage and the supplying passage is cut off from the second fluid supplying passage, and a second position wherein the nozzle side passage is cut off from the valve side passage of the first fluid supplying passage and the supplying passage is connected to the second fluid supplying passage; and a check valve provided to the supplying passage for preventing flow from the switching passage side to the supplying passage side.

In this connection, the pump connector can be composed of a casing mounted to the operating unit to which are connected a nozzle side and a valve side passages in the first fluid supplying passage and a second fluid supplying passage, and a fluid pumping means connecting unit mounted in the casing to be detachably connected the fluid pumping means and having a switching passage and a supply passage provided with a check valve. The fluid pumping means connecting unit may be switched by its rotational operation of a predetermined angle within the casing to select the switching passage between a first position wherein the nozzle side passage is communicated to the valve side passage of the first fluid supplying passage, while the supplying passage is cut off from the second fluid supplying passage, and a second position wherein the nozzle side passage is cut off from the valve side passage of the first fluid supplying passage, while the supplying passage is connected to the second fluid supplying passage. In this case, the fluid pumping means connecting unit can be installed with click means for retaining these two selection positions for producing a suitable operation feeling. By constructing the fluid pumping means connecting unit movable along the axial line direction by a predetermined length within the casing and being provided a connecting passage, switching to a third selected position is further available to connect the valve side passage of the first fluid supplying passage with the second fluid supplying passage, while cutting off the nozzle side passage, thus enabling fluid to be supplied in four modes.

These and other objects, configurations, and advantages and the like of the present invention will become more apparent from the embodiments described below with reference to the drawings. It is needless to say that the present invention is not to be interpreted so as to be restricted to these embodiments.

DETAILED DESCRIPTION OF THE INVENTION

Figure 1:
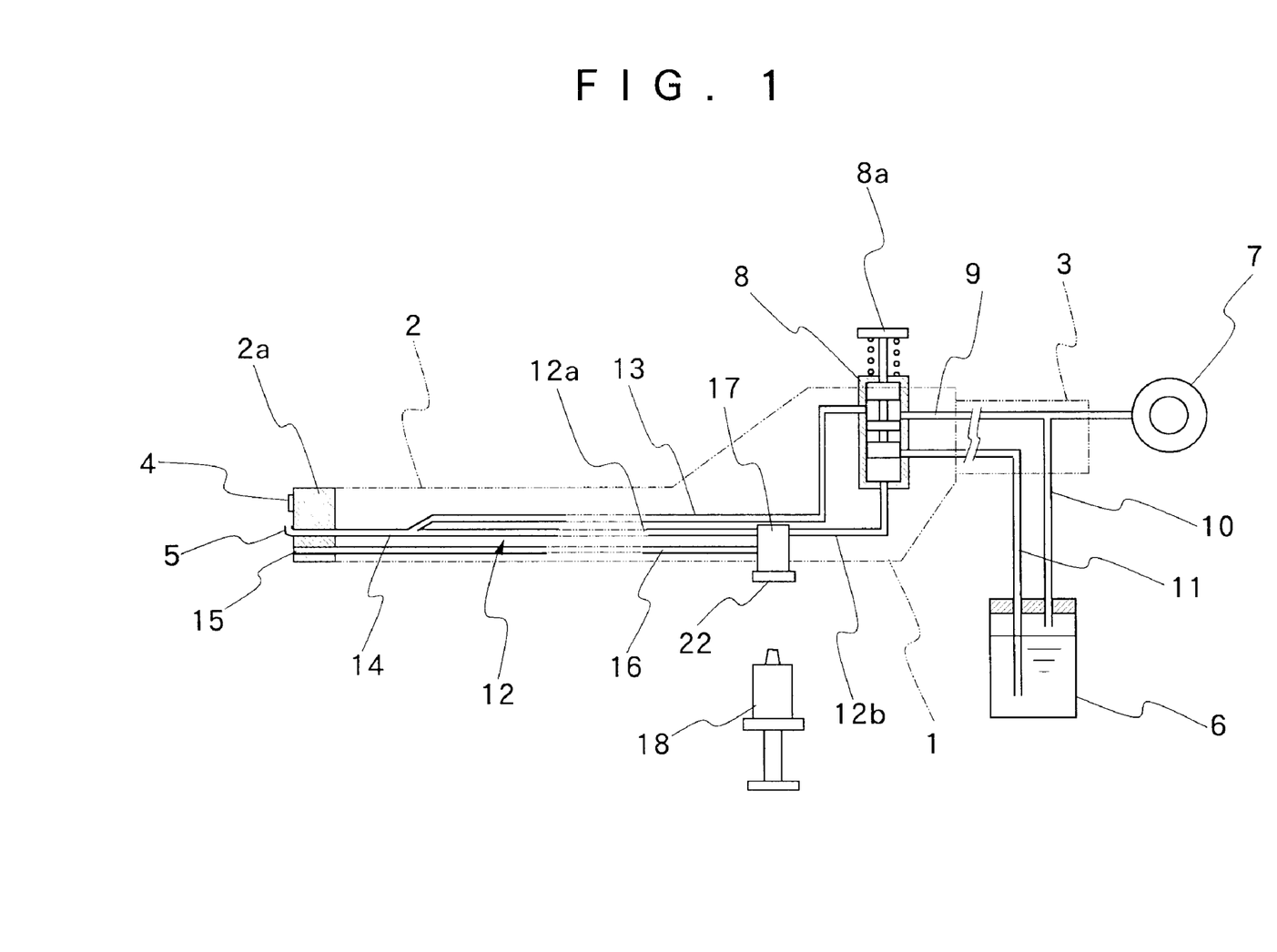
FIG. 1 is a schematic configuration diagram of the fluid supplying apparatus of the endoscope, illustrating an embodiment of the present invention.

An embodiment of the present invention will now be described with reference to the drawings. First, FIG. 1 shows the schematic configuration of the fluid supplying apparatus of an endoscope. As shown in the Figure, the endoscope has an insertion portion 2 to be inserted into a body cavity and the like formed continuing from the operating unit 1, and a universal cord 3 is extended from the operating unit 1. An observation window mounted with a lens surface 4 (an object lens or a cover glass thereof) is mounted to a distal end 2a of the insertion portion 2, and a spraying nozzle 5 for cleaning liquids is provided facing this lens surface 4.

Washing water from a washing water tank 6 and pressurized air from an air pump 7 are selectively supplied to the spraying nozzle 5. A control valve 8 is provided to the operating unit 1, in order to control the pressurized air and washing water. The control valve 8 has an operating button 8a provided with an opening communicated to atmosphere (not shown), and the operating button 8a can be operated with fingers. In the state that the operating button 8a is not touched, the air from the air pump 7 is discharged into the atmosphere. Also, when the atmospheric discharge opening is closed, the pressurized air is supplied. Pressing the operating button 8a down allows water to be supplied from the washing water tank 6. The configuration of the control valve 8 is known, so drawings and description of the specific configuration thereof is omitted.

The air conduit 9 from the air pump 7 is connected to the control valve 8, and also diverged to a pressurized air conduit 10 for pressurizing the washing water tank 6. The water supplying conduit 11 from the washing water tank 6 is also connected to the control valve 8. A water supplying passage 12 and air supplying passage 13 are connected to the control valve 8. The water supplying passage 12 and air supplying passage 13 are joined near the distal end portion of the insertion portion 2 to form a joined passage 14, and this passage 14 is connected to the spraying nozzle 5. It is possible to construct the water supplying passage and air supplying passage to be independently connected to separate nozzles.

The spraying nozzle 5 is facing the direction of the lens surface 4. i.e., the direction across the axial line of the insertion portion. The observation window has an observation field of view in the extrapolated direction of the insertion portion 2. In order to wash off stain, such as body fluid adhered to the body cavity or spray on drug fluid or the like, a spray aperture should be facing the direction of the observation field of view, that is, to the forward direction of the insertion portion 2. Accordingly, an aperture 15 is opened at the distal end 2a in the direction forward to the insertion portion 2, so as to serve as a jet spray aperture. A liquid supplying passage 16 connected to the jet spray aperture 15 consists of a different system from the cleaning of the lens surface 4. This liquid supplying passage 16 is extended to the operating unit 1, and is connected to an auxiliary fluid supplying portion 17 serving as the pump connector provided to the operating unit 1. Also, the water supplying passage 12 is connected to the auxiliary fluid supplying portion 17 near the mounting position of the control valve 8 within the operating unit 1. Accordingly, the water supplying passage 12 is divided to the nozzle side passage 12a and valve side passage 12b at the position of the auxiliary fluid supplying portion 17.

A syringe 18 or other fluid pumping means is detachably connected to the auxiliary fluid supplying portion 17, by means of a known lure lock mechanism or the like, for example. Accordingly, the nozzle side passage 12a of the water supplying passage 12 connecting to the spraying nozzle 5 is the first fluid supplying passage, and the liquid supplying passage 16 connected to the jet spray aperture 15 is the second fluid supplying passage. Then, an auxiliary fluid supply portion 17 is a valve for connecting the valve side passage 12b to a nozzle side passage 12a or a liquid supply passage 16. Accordingly, when the syringe 18 is disconnected, washing water can be supplied from the washing water tank 6 to the spraying nozzle 5. Also, in the event that the syringe 18 is connected, fluid within the syringe 18 can be sprayed from the spraying nozzle 5, and fluid can be sprayed from the jet spray aperture 15 via the liquid supplying passage 16. Accordingly, selection may be from three modes of fluid transporting states.

Figure 2:
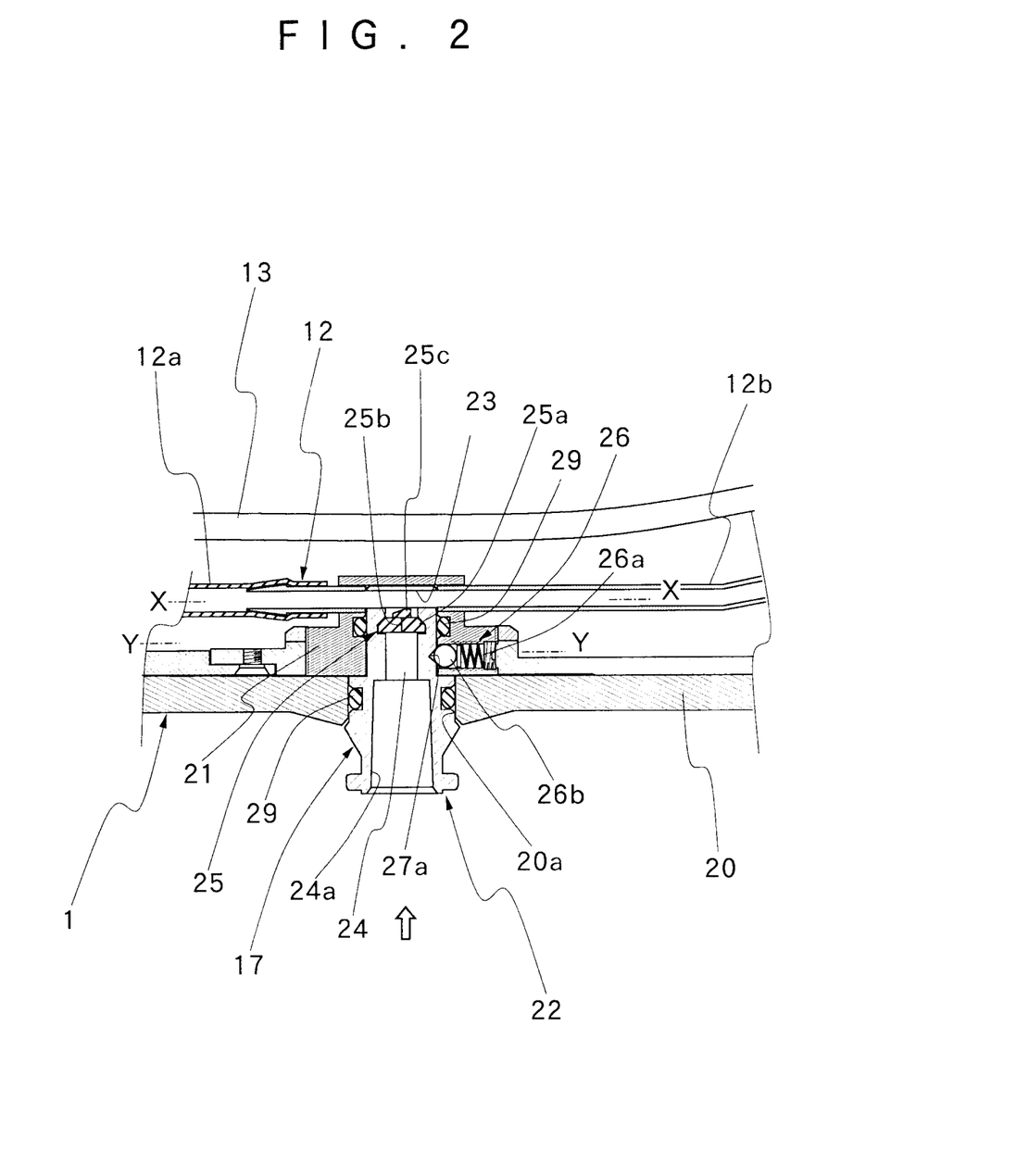
FIG. 2 is a cross-sectional view illustrating the configuration of an auxiliary fluid supplying portion.
Figure 3:
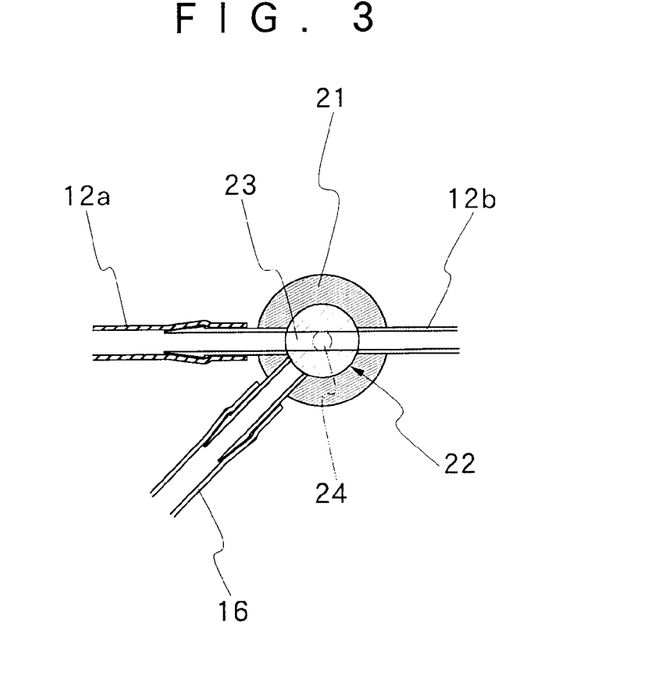
FIG. 3 is a cross-sectional view along line X—X in FIG. 2.
Figure 4:
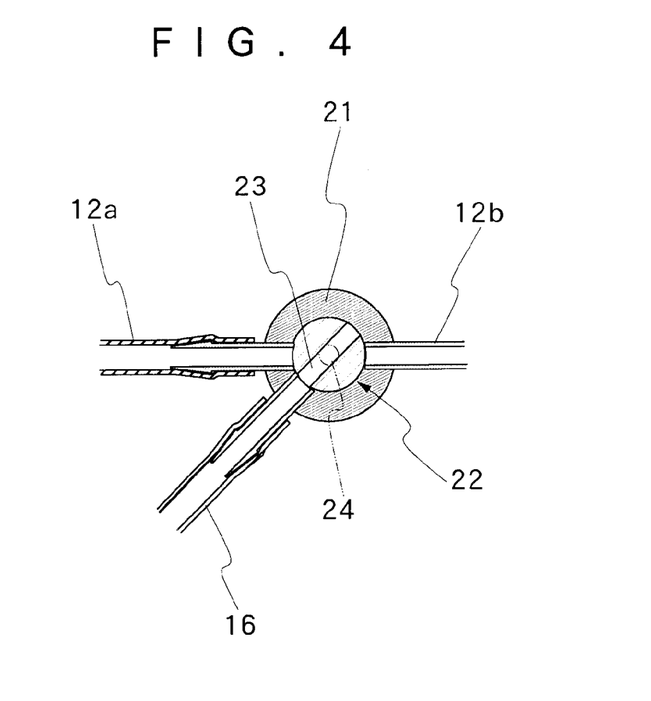
FIG. 4 is a cross-sectional view illustrating an operation state different to that shown in FIG. 3.

FIG. 2 shows a cross-section at the position including the auxiliary fluid supplying portion 17 of the operating unit 1. As can be clearly understood from this Figure, an opening 20a is formed to the housing 20 of the operating unit 1, and a casing 21 for splitting the fluid passage is mounted at a position facing to this opening 20a of the housing 20. One side of the casing 21 is closed off, the nozzle side passage 12a and valve side passage 12b of the water supplying passage 12 are connected near this closed off portion as shown in FIG. 3 and FIG. 4, and the liquid supplying passage 16 is also connected to the casing 21. The auxiliary fluid supplying portion 17 is mounted, inserted into the casing 21. The syringe 18 is detachably connected to this auxiliary fluid supplying portion 17.

The other end of the auxiliary fluid supplying portion 17 is mounted into the opening 20a of the housing 20 of the operating unit 1, and is protruded outwards from the operating unit 1 by a predetermined length. A switching passage 23 is provided to the auxiliary fluid supplying portion 22, passing through the direction orthogonal to the axial line thereof, near the inserted end to the casing 21 thereof. Also, a supplying passage 24 is provided to feed fluid from syringe 18 serving as the fluid pumping means, the supplying passage 24 being communicated at one end to the switching passage 23 and opening to the outer side of the operating unit 1 of the auxiliary fluid supplying portion 22 at the other end. The base side of this supplying passage 24 has a greater diameter, and this greater diameter portion serves as the connecting portion 24a to the syringe 18. Further, a check valve 25 is mounted to a position before the connecting portion to the switching passage 23 on this supplying passage 24. The check valve 25 has a main plate 25a formed of a rubber plate with a slit 25b, wherein a tongue 25c is provided to the side of the main plate 25a facing the switching passage 23, so as to act in the direction of closing the slit 25b. The check valve 25 acts such that pressurized fluid can be caused to flow from the supplying passage 24 side to the switching passage 23 side, but fluid can not flow backward from the switching passage 23 side to the supplying passage 24, even if the pressure of the switching passage 23 side is higher than the supplying passage 24 side.

The auxiliary fluid supplying portion 22 is rotatable in both directions at a certain angle within the casing 21. At the position shown in FIG. 3, the switching passage 23 has been connected to the nozzle side passage 12a and valve side passage 12b of the water supplying passage 12. In the state of FIG. 3, the switching passage 23 is in a state of not being connected to the liquid supplying passage 16. This is the first position. Then, when rotation is made to the position shown in FIG. 4, the switching passage 23 is not connected to either the nozzle side passage 12a or valve side passage 12b, i.e., a state wherein the spraying nozzle 5 and control valve 8 on the water supplying passage 12 are cut off. Also, the switching passage 23 is connected to the liquid supplying passage 16, and this is the second position.

Figure 5:
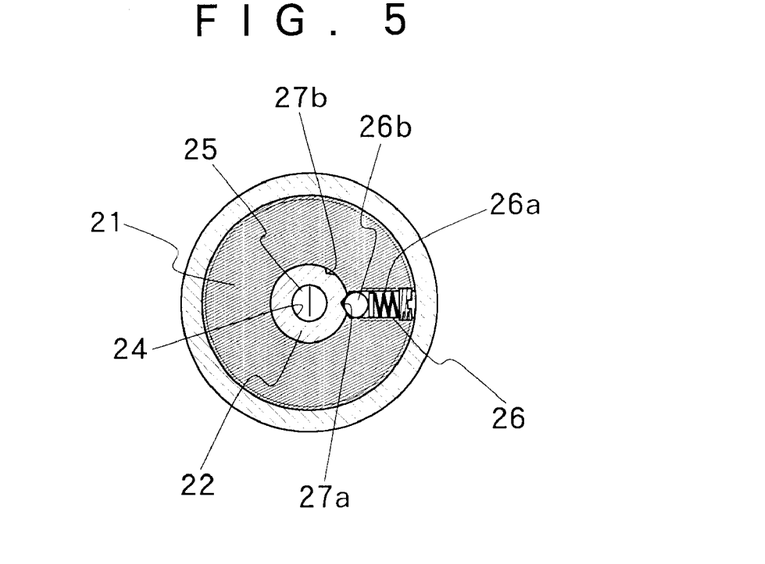
FIG. 5 is a cross-sectional view along line Y—Y in FIG. 2.
Figure 6:
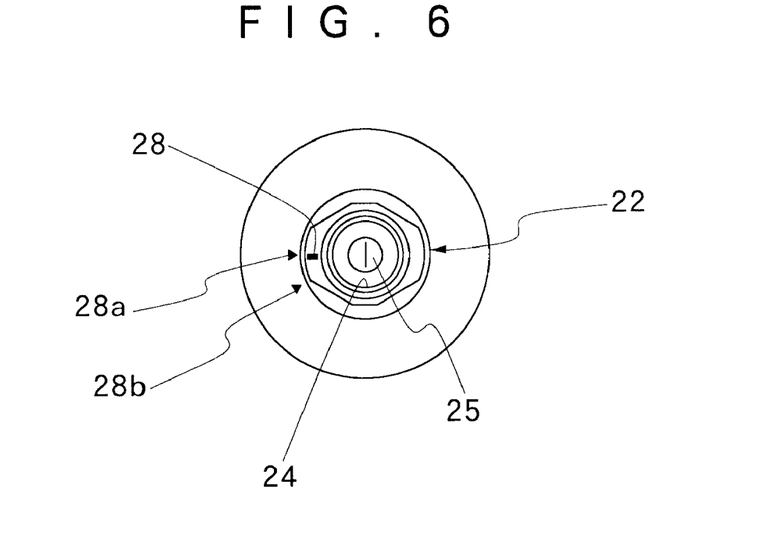
FIG. 6 is an external view as viewed form the direction of the arrow shown in FIG. 2.

In order to fixedly hold the auxiliary fluid supplying portion 22 at the above first and second positions, as shown in FIG. 5, a click member 26 made of a click ball 26b pressed by a click spring 26a is provided to the casing 21, and click grooves 27a and 27b are formed at two places on the outer periphery of the auxiliary fluid supplying portion 22. Accordingly, at the time that the click ball 26b of the click member 26 fits with the click groove 27a, the auxiliary fluid supplying portion 22 is held at the first position, while fitting with the click groove 27b, the auxiliary fluid supplying portion 22 is held at the second position. Also, as can be understood from FIG. 6, indicators 28a and 28b are provided to the surface of the housing 20 of the operating unit 1, indicating whether the auxiliary fluid supplying portion 22 is at the first position or second position. The selected position can be recognized depending on whether the reference display portion 28 of the auxiliary fluid supplying portion 22 is at a position matching the indicator 28a or at a position matching the indicator 28b.

Figure 7:
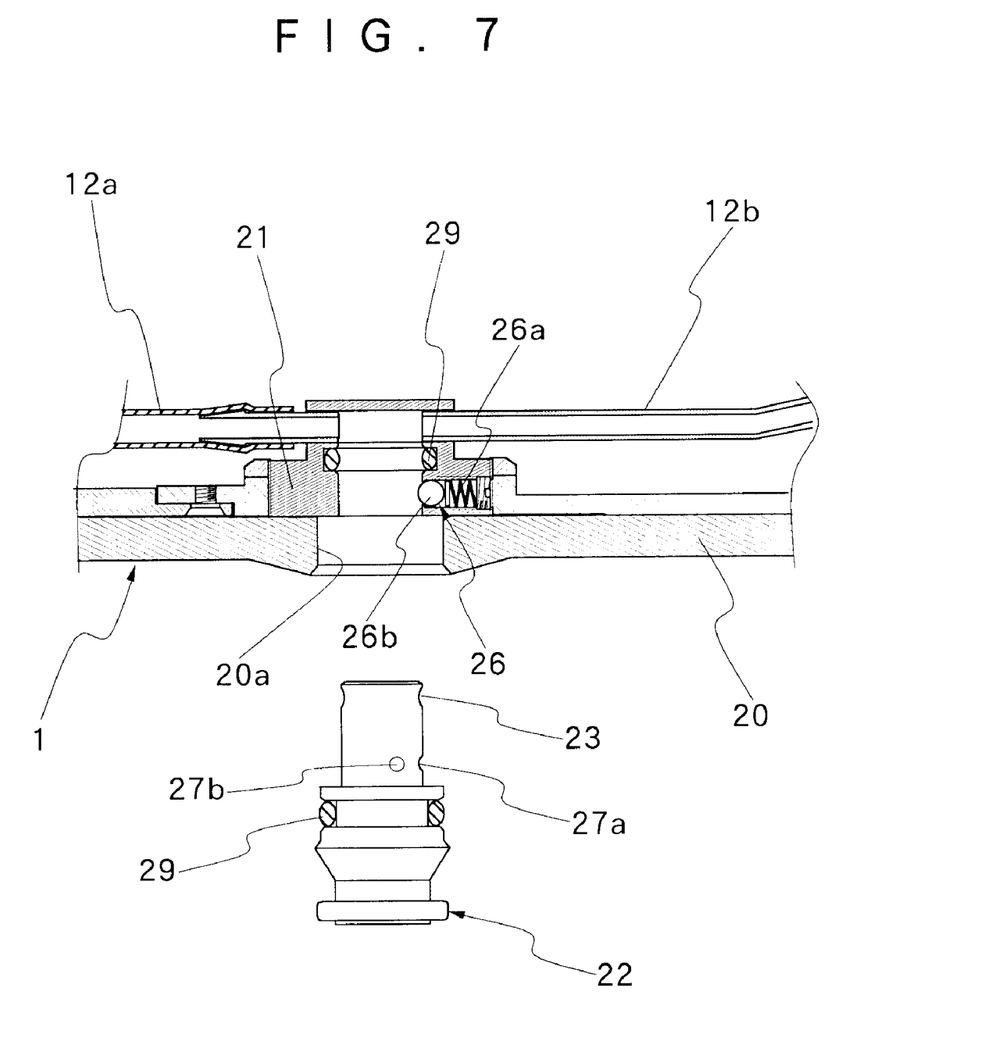
FIG. 7 is a cross-sectional view illustrating the state of the auxiliary pumping unit detached as with FIG. 2.

Now, as shown in FIG. 7, the auxiliary fluid supplying portion 22 is detachably mounted to the operating unit 1. Seal rings 29 and 29 are mounted between the outer periphery of the auxiliary fluid supplying portion 22 and the inner surface of the casing 21 in the opening 20a of the housing 20 of the operating unit 1, thereby holding the auxiliary fluid supplying portion 22 in a stable manner in the mounted state, and also so that the contaminant does not enter into the operating unit 1. Also, at the time of inserting the auxiliary fluid supplying portion 22 into the casing 21, the seal rings 29 are deformed to a certain extent, consequently this functions as dropout prevention by the elasticity so that the auxiliary fluid supplying portion 22 does not drop out from the operating unit 1.

Due to a configuration such as above, the fluid supplying can be selected and switched in the following states. First is the state wherein washing water is pumped from the washing water tank 6 via the water supplying passage 12 to the spraying nozzle 5 at a pressure stipulated by the air pump 7. Also, washing water can be pumped to the spraying nozzle 5 from the syringe serving as the fluid pumping means at a desired pressure. Also, a desired kind of fluid can be supplied from the liquid supplying passage 16 to the jet spray aperture 15, at a desired pressure.

Now, with the auxiliary fluid supplying portion 22 held in the first position shown in FIG. 3, the nozzle side passage 12a of the water supplying passage 12 is connected to the valve side passage 12b via the switching passage 23. Also, the supplying passage 24 is connected to the switching passage 23 via the check valve 25. However, connection between the water supplying passage 12 and the water supplying conduit 11 is cut off by the control valve 8 unless the control valve 8 is operated. Also, the flow from the water supplying passage 12 side to the supplying passage 24 is blocked by the check valve 25, if the pressure is high at the water supplying passage 12 side.

Now, operation of the control valve 8, by pressing the operating button 8a, causes connection of the water supplying conduit 11 with the water supplying passage 12 and feeds air pressure from the air pump 7 into the washing water tank 6 via the pressurized air conduit 10, whereby washing water is supplied within the water supplying conduit 11 at a pressure according to the air pressure, and washing water being supplied to the water supplying passage 12 from the water supplying conduit 11 via the control valve 8. Here, the valve side passage 12b on the water supplying passage 12 is connected to the nozzle side passage 12a via the switching passage 23, so washing water is supplied to the spraying nozzle 5 from the water supplying passage 12 via the joined passage 14. Consequently, stain adhered to the lens surface 4 can be washed off. Subsequently, the operating button 8a is returned, the connection between the water supplying conduit 11 and the water supplying passage 12 is cut off, and the atmospheric releasing opening of the operating button 8a is held at a blocked state. Thus, pressurized air from the air pump 7 flows through the air conduit 9 to the air supplying passage 13, and pressurized air can be blown on the lens surface 4 from the spraying nozzle 5. Thus, droplets and the like on the lens surface 4 can be removed by the action of the air pressure, and the lens surface 4 becomes to a clean state.

When the washing water tank 6 is used as the supplying source for washing water, the pressure of the washing water sprayed from the spraying nozzle 5 depends on the pressure of the air pump 7. However, there is stubborn soiling and the like which cannot be removed with this pressure. At such times, high-pressure washing water can be supplied to the lens surface 4. To this end, the syringe 18 is connected to the auxiliary fluid supplying portion 22, and the control valve 8 cuts off the connection between the water supplying conduit 11 and the water supplying passage 12. Then, the syringe 18 filled with the washing water is manually pressed the syringe 18 down supplies washing water is supplied from the syringe 18 to the supplying passage 24. Because the syringe 18 is manually operated, arbitrary pressure can be generated with adjusting the pressing force. The check valve 25 is opened by the pressure to feed washing water into the water supplying passage 12 from the switching passage 23. By operating the syringe 18, washing water immediately sprays from the spraying nozzle 5 at a pressure corresponding to the pressing pressure, because washing water fills at least the entire water supplying passage 12 after supplying washing water from the washing water tank 6, and also fills the joined passage 14 immediately after this fluid supplying, while the end of the valve side passage 12b is cut off by the control valve 8. Consequently, washing water can be sprayed onto the lens surface 4 at a desired pressure, and stubborn soiling and the like can be removed in a sure manner.

The spraying nozzle 8 is for supplying washing water to the lens surface 4. On the other hand, washing water for washing off stain, such as body fluids adhered to the body cavity wall, can be sprayed from the jet spray aperture 15, and also fluids with uses other than that of washing water, e.g., various drug fluids containing coloring agents, can also be sprayed. For supplying a desired fluid to this jet spray aperture 15, the auxiliary fluid supplying portion 22 is switched to the second position, shown in FIG. 4. This operation can be performed by simply by rotating the auxiliary fluid supplying portion 22 by a predetermined angle around the axis. At this second position, connection between both the nozzle side and valve side passages 12a and 12b of the of the water supplying passage 12 with the switching passage 23 is cut off, and the switching passage 23 is connected only with the liquid supplying passage 16. Of course, the connection between the switching passage 23 and the supplying passage 24 is cut off by the operation of the check valve 25. So even in the event that the pressure within the liquid supplying passage 16 is high, flow is prevented in the reversed direction from the liquid supplying passage 16 side to the supplying passage 24 side.

For example, a syringe 18 filled with a desired fluid such as washing water or drug fluid or the like is mounted to the auxiliary fluid supplying portion 22. Pressuring the syringe 18 by manual operation causes the check valve 25 to open due to the pressure of the fluid within the syringe 18, and fluid is supplied to the liquid supplying passage 16 from the supplying passage 24 via the switching passage 23. Accordingly, this fluid is sprayed from the jet spray aperture 15. Now, unlike the spraying nozzle 5, the jet spray aperture 15 is arranged so as to be able to spray fluids in the forward direction of the insertion portion 2, so washing water or drug fluid or the like can be sprayed into the body cavity walls being observed in a sure manner. Consequently, cleaning of the body cavity wall to be observed, or dispersion of drug fluid for inspection, can be performed smoothly.

Now, there is the need to clean the endoscope after each time it is used. Also, the inside of the above-descried fluid supplying apparatus must be completely cleaned. The auxiliary fluid supplying portion 22 has the switching passage 23, supplying passage 24, and check valve 25 integrally assembled, and further this can be easily detached from the casing 21. Accordingly, as shown in FIG. 7, by removing the auxiliary fluid supplying portion 22 from the operating unit 1, the nozzle side passage 12a, the valve side passage 12b of the water supplying passage 12, and the liquid supplying passage 16 are opened from the casing 21, and also the diameter within these passages is approximately uniform over the entire length, thereby cleaning may be easily perform by inserting a cleaning brush from the casing 21 into each passage. Incidentally, the length of the valve side passage 12b of the water supplying passage 12 is short. There is little possibility that the interior thereof will be soiled, so a check valve for opening the passage when the control valve 8 side is high pressure can be provided near the connecting side thereof to the control valve 8, for example. Thus, at the time of cleaning the lens surface 4, washing water can be supplied from the syringe 18 with the water supplying conduit 11 and the water supplying passage 12 connected with the control valve 8.

Figure 8:
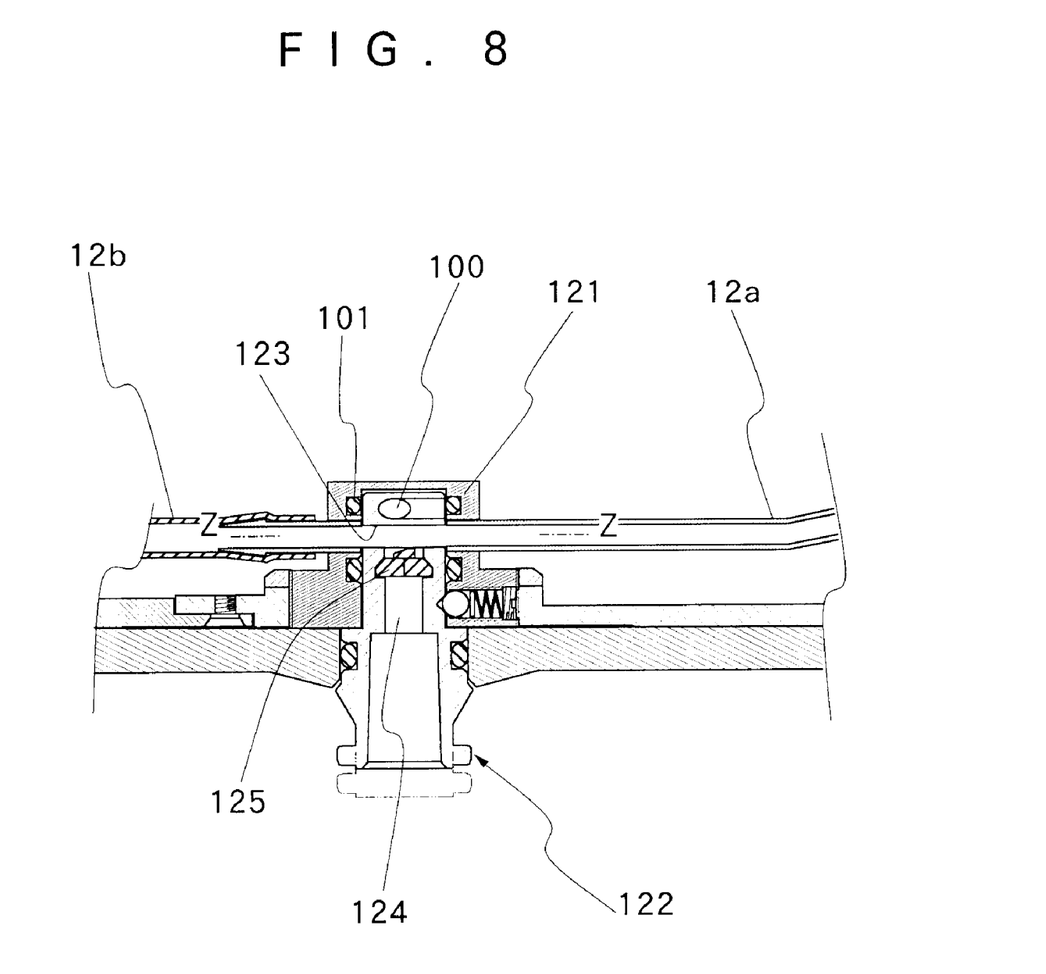
FIG. 8 is a cross-sectional view of an auxiliary fluid supplying portion illustrating a second embodiment of the present invention.
Figure 9:
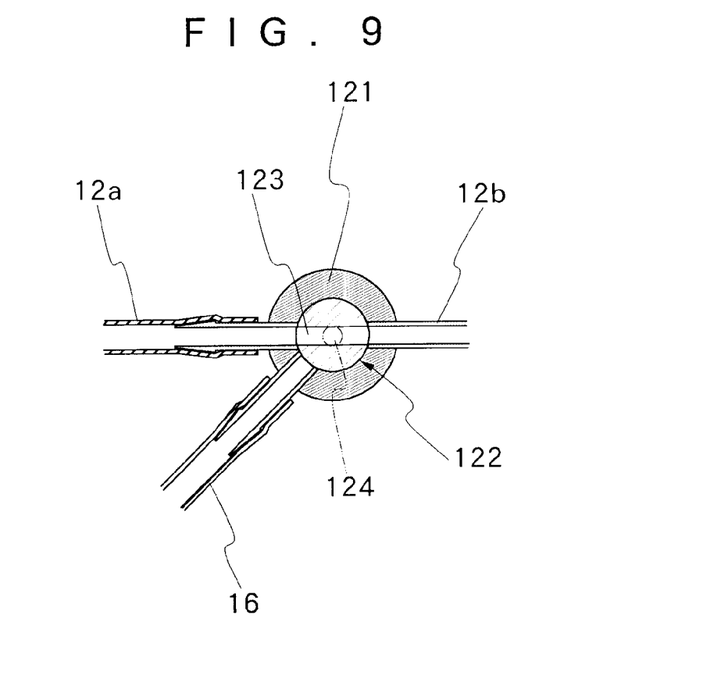
FIG. 9 is a cross-sectional view along line Z—Z in FIG. 8.
Figure 10:
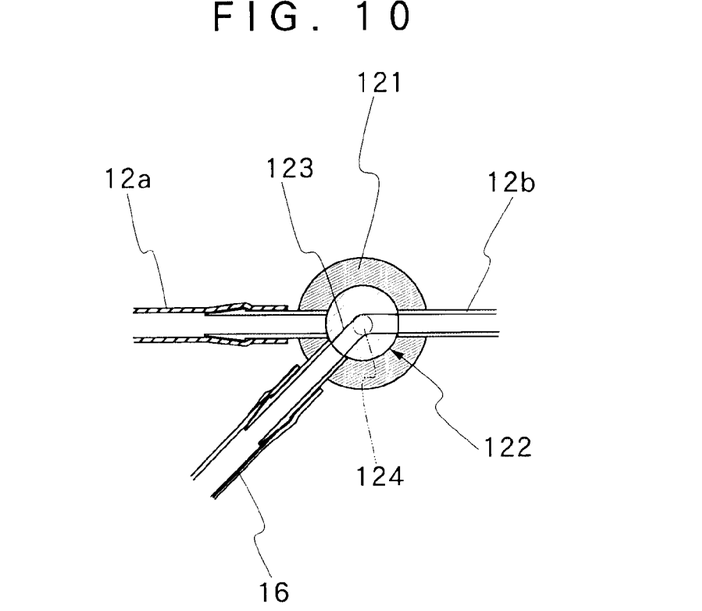
FIG. 10 is a cross-sectional view illustrating an operation state different to that shown in FIG. 9.

Next, FIG. 8 through FIG. 10 illustrate a second embodiment of the present invention. In this embodiment, in addition to the three modes of fluid supply which can be selected in the above first embodiment, further washing water from the washing water tank 6 can be supplied to the jet spray aperture 15.

For this purpose, the configuration is adapted such that an auxiliary fluid supplying portion 122 is provided with a supplying passage 124, a switching passage 123 and a check valve 125 provided therebetween, along with a connection passage 100 which is placed at further fore end than the position where the switching passage 123 is provided. Also, a seal ring 101 is provided between the formation portion of the switching passage 123 on the periphery of the auxiliary fluid supplying portion 122 and the formation position of the connection passage 100. On the other hand, as shown in FIG. 9 and FIG. 10, the nozzle side passage 12a and valve side passage 12b of the water supplying passage 12 and the liquid supplying passage 16 are opened at the casing 121, and the depth thereof is deeper than the above-described first embodiment for providing the connection passage 100 to the auxiliary fluid supplying portion 122.

The connection passage 100 is for connecting the valve side passage 12b of the water supplying passage 12 and the liquid supplying passage 16. As indicated by solid lines in FIG. 8, the state wherein the auxiliary fluid supplying portion 122 is pressed into the casing 121 is shown in FIG. 9, and this exhibits exactly the same functions as the first embodiment. Then, as shown in FIG. 8 with the phantom lines, by replacement of the auxiliary fluid supplying portion 122 in the direction of being extracted from the casing 121 by a predetermined length, the nozzle side passage 12a of the water supplying passage 12 is brought to the state of being cut off from the valve side passage 12b, as shown in FIG. 10, but the valve side passage 12b is connected to the liquid supplying passage 16 via the connection passage 100. Accordingly, pressing the operating button 8a of the control valve 8 in this state to connect the water supplying conduit 11 and the valve side passage 12b of the water supplying passage 12, washing water from the washing water tank 6 supplied from the connection passage 100 is supplied to the liquid supplying passage 16. Accordingly, water is sprayed ahead of the insertion portion 2 from the jet spray aperture 15, i.e., in the direction of the observation field of view from the observation window. Thus, the task of washing off stain of the body cavity wall can be performed even without using a syringe 18.

What is claimed is:

1. A fluid supplying apparatus for an endoscope, which comprises:

an observation window provided at a distal end portion of an insertion portion;

a nozzle for spraying at least a cleaning liquid toward said observation window;

a first fluid supplying passage connected to said nozzle;

a jet spray aperture formed to said distal end portion for spraying fluid in forward direction of said insertion portion;

a second fluid supplying passage connected to said jet spray aperture;

a control valve provided within a operating unit provided connected to said insertion portion, to which said first fluid supplying passage is connected;

a casing for dividing said first fluid supplying passage into a nozzle side passage and a valve side passage, and to which said second fluid supplying passage is connected;

a pump connector, provided within said casing, for detachably mounting a fluid pumping means and being formed a supplying passage for flowing fluid from said fluid pumping means;

a switching passage provided to said pump connector, said switching passage being capable of switching between a first position wherein said nozzle side passage is connected to a valve side passage of said first fluid supplying passage and said supplying passage is cut off from said second fluid supplying passage, and a second position wherein said nozzle side passage is cut off from said valve side passage of said first fluid supplying passage and said supplying passage is connected to said second fluid supplying passage; and a check valve provided to said supplying passage for preventing flow from said switching passage side to said supplying passage side.

2. A fluid supplying apparatus for an endoscope according to claim 1, wherein said control valve is connected to an air conduit for supplying pressurized air from an air pump, and a water supply conduit from a washing water tank being pressurized by said air pump, and said first fluid supplying passage is constructed to be connected to and cut off from said water supplying conduit by operation of said control valve.

3. A fluid supplying apparatus for an endoscope according to claim 1, wherein said casing is provided within a housing of said operating unit, said pump connector is detachably mounted to said casing, and said pump connector is protruded externally from said housing, at least at a portion where said fluid pumping means is connected to.

4. A fluid supplying apparatus for an endoscope according to claim 3, wherein seal members are provided between said pump connector and said casing and housing, said seal member functioning being fixedly held to said pump connector to said casing.

5. A fluid supplying apparatus for an endoscope according to claim 1, wherein said pump connector is swichable between said two positions by rotational operation of both directions of a predetermined angle.

6. A fluid supplying apparatus for an endoscope according to claim 5, wherein said pump connector comprises click means for holding said first position and said second position.

7. A fluid supplying apparatus for an endoscope according to claim 1, wherein said pump connector is further allowed to move in the axial line direction at a predetermined length within said casing and also is provided a connecting passage, thereby giving a third position to be connected said valve side passage of said first fluid supplying passage with said second fluid supplying passage, and also cutting off said nozzle side passage.

8. A fluid supplying apparatus for an endoscope according to claim 1, wherein a syringe for pumping washing water at least and a syringe for pumping fluid drug are detachably connected to said pump connector.

* * * * *